US008000948B2

(12) United States Patent
Bugrim et al.

(10) Patent No.: US 8,000,948 B2
(45) Date of Patent: *Aug. 16, 2011

(54) METHODS FOR IDENTIFYING COMPOUNDS FOR TREATING DISEASE STATES

(75) Inventors: Andrej Bugrim, St. Joseph, MO (US); Tatiana Nikolskaya, Portage, IN (US); Aleksander Markov, Moscow (RU)

(73) Assignee: Genego, Inc., Encinitas, CA (US)

( * ) Notice: Subject to any disclaimer, the term of this patent is extended or adjusted under 35 U.S.C. 154(b) by 257 days.

This patent is subject to a terminal disclaimer.

(21) Appl. No.: 10/518,103

(22) PCT Filed: Jun. 18, 2003

(86) PCT No.: PCT/US03/19325
§ 371 (c)(1),
(2), (4) Date: Oct. 14, 2005

(87) PCT Pub. No.: WO03/107545
PCT Pub. Date: Dec. 24, 2003

(65) Prior Publication Data
US 2006/0052939 A1    Mar. 9, 2006

Related U.S. Application Data

(60) Provisional application No. 60/389,474, filed on Jun. 18, 2002.

(51) Int. Cl.
*G06G 7/48* (2006.01)
(52) U.S. Cl. ........................................................ 703/11
(58) Field of Classification Search ........................ None
See application file for complete search history.

(56) References Cited

U.S. PATENT DOCUMENTS

| | | | |
|---|---|---|---|
| 6,074,616 A * | 6/2000 | Buechler et al. | 422/104 |
| 2002/0159625 A1 | 10/2002 | Elling | |
| 2003/0224363 A1 | 12/2003 | Park et al. | |
| 2003/0233218 A1* | 12/2003 | Schilling | 703/11 |
| 2006/0235624 A1 | 10/2006 | Nikolskaya et al. | |

FOREIGN PATENT DOCUMENTS

| WO | WO-00/50889 | 8/2000 |
|---|---|---|
| WO | WO-01/13105 | 2/2001 |

OTHER PUBLICATIONS

Nakao et al. (Genomescale gene expression analysis and pathway reconstruction in KEGG, Genome Informatics, 10:94-103, 1999).*
Karp et al. (Trends in biotechnology, vol. 17, p. 275-281, 1999).*
Johansen et al. (Expert Opinion in Therapeutic Targets, vol. 11, No. 2, p. 219-234, 2007).*
KEGG table of contents as of Feb. 1999(online resource, [http://web.archive.org/web/19990203053246/www.genome.ad.jp/kegg/kegg2.html]).*
Kuffner et al. (Bioinformatics, vol. 16, No. 9, p. 825-836, 2000).*
Kumar (Reactive and Functional Polymers, vol. 46, p. 1-27, 2000).*
Tile D4 of the Boerhinger Biochemical pathways map (Roche Applied Science, 1993 Online [http://www.expasy.org/cgi-bin/show_image?D4&up]).*
Okubo et al. (Nature Genetics, vol. 2, p. 173-179, Nov. 1992).*
Ishizuka et al. (Information processing society of Japan, vol. 91, p. 73-80, Sep. 27, 2000).*
Takai-Igarashi et al. (In Silico Biology, vol. 1, p. 129-146, 1999).*
Forst et al. (Journal of Computational Biology vol. 6, Nos. 3/4, 1999, pp. 343-360).*
van Heyningen (Molecular Medicine, vol. 3, No. 4, Apr. 1997. 231-237).*
Boot et al., Arterioscler Thromb Vasc Biol. (1999) 19(3):687-694.
Chajara et al., Atherosclerosis (1996) 125(2):193-207.
Haase and Bartold, J. Periodontol. (2001) 72(3):341-348.
Hovingh and Linker, J. Biol. Chem. (1970) 245:6170-6175 (EC No. 4.2.2.7).
International Search Report for PCT/US03/19325, mailed on May 26, 2004, 2 pages.
Khan et al., Electrophoresis (1999) 20(2):223-229.
Kirkpatrick et al., Gene (1995) 153(2):147-154.
Kuroda et al., J. Dermatol. Sci. (2001) 26(2):156-160.
Lark et al., Fed Proc. (1985) 44(2):394-403.
Lindvall, Europ. Neurol. (1991) 31(Suppl. 1):17-27.
Luke and Prehm, Biochem. J. (1999) 343(Pt. 1):71-75.
Mookerjea, Can J. Biochem. (1978) 56(7):746-752.
NCBI Online Database, Accession Nos. AAE10146-AAE10153.
NCBI Online Database, Accession Nos. AAE13758-AAE13770.
NCBI Online Database, Accession Nos. AAE67749-AAE67785.
Neuger et al., Atherosclerosis (2001) 157(1):13-21.
Osawa et al., Cells Tissues Organs (2000) 167(1):9-17.
Papakonstantinou et al., Atherosclerosis (1998) 138(1):79-89.
Papakonstantinou et al., PNAS USA (1995) 92(21):9881-9885.
Recklies et al., Biochem. J. (2001) 354(Pt. 1):17-24.
Saveliev et al., Int J. Biol. (1997) 41(6):801-808.
Schaefer et al., J. Cell Sci. (1996) 109(Pt. 2):479-488.
Scharnagl et al., Lab Invest. (1999) 79(10):1271-1286.
Selkov et al., Gene (1997) 197:GC11-26.
Selkov et al., PNAS USA (2000) 97(7):3509-3514.
Semino et al., PNAS USA (1996) 93(10):4548-4553.
Shackelton et al., J. Biol. Chem. (1995) 270(22):13076-13083.
Shyjan et al., J. Biol. Chem. (1996) 271(38):23395-23399.
Stanley et al., J. Biol. Chem. (1995) 270(10):5077-5083.
U.S. Appl. No. 60/299,040, filed Jun. 18, 2001.
Vellacott and Balfour, Br. Med J. (1978) 2(6138):699.
Volker et al., J. Histochem. Cytochem. (1991) 39(10):1385-1394.
Watanabe and Yamaguchi, J. Biol. Chem. (1996) 271(38):22945-22948.
Zimmermann et al., Biochim. Biophys. Acta (2000) 1484(2-3):316-324.
Covert et al., Trends in Biochemical Sciences (2001) 26(3):179-186.
Notice of Rejection for Japanese Patent Application No. 2004-514229, mailed on Jun. 23, 2009, 3 pages.
GOLD Database, retrieved online at http://wit.integratedgenomics.com/GOLD/, date retrieved on May 23, 2008.

* cited by examiner

*Primary Examiner* — Karlheinz R Skowronek
(74) *Attorney, Agent, or Firm* — Morrison & Foerster LLP

(57) ABSTRACT

The process of System Reconstruction is used to integrate sequence data, clinical data, experimental data, and literature into functional models of disease pathways. System Reconstruction models serve as informational "skeletons" for integrating various types of "high throughput" data.

18 Claims, 5 Drawing Sheets

Figure 1. An overview of the process of Functional Reconstruction

Figure 2. A fragment of reconstruction of human amino acid metabolism. Rectangles represent pathways, balloons contain lists of diseases associated with pathways. Pathways are color-coded for subcellular localization. The map is an interactive interface to the database.

Figure 4 Chitotriosidase function in atherogenesis

Figure 4A - chitotriosidase activity is absent
Figure 4B - chitotriosidase activity is present

METHODS FOR IDENTIFYING COMPOUNDS FOR TREATING DISEASE STATES

CROSS-REFERENCE TO RELATED APPLICATIONS

This application is the national phase of PCT application PCT/US03/19325 having an international filing date of Jun. 18, 2003, which claims the benefit of U.S. Provisional Application No. 60/389,474, filed Jun. 18, 2002. The contents of these documents are incorporated herein by reference.

FIELD OF THE INVENTION

The present invention relates to bioinformatics technologies. More specifically, the present invention relates to the technology of System Reconstruction. The present invention further relates to methods for elucidating metabolic pathways involving chitinase.

BACKGROUND

Recent progress in sequencing technology has generated a vast amount of genomic data. According to the GOLD database, there are more than 300 genomic projects currently completed or under development. Seventy-nine complete or partially complete genomes are available through the public ERGO system. In order to handle this wealth of information, several powerful bioinformatics systems have been developed. The WIT Project was instituted to develop a framework for the comparative analysis of genomic sequence data, focusing largely on the development of metabolic models for sequenced organisms. The analysis of the genomes involves several distinct, but complementary efforts. The first is a determination of open reading frames (ORFs). The second, often called annotation, is the assignment of functions to genes. The third is the creation of functional models for metabolic and regulatory networks of the sequenced genomes, referred to as reconstruction.

Metabolic reconstruction for bacterial and archaeobacterial genomes has been carried out. (E. Selkov et al., Proc. Natl. Acad. Sci. U.S.A. 2000 Mar. 28; 97(7):3509-14). In contrast, metabolic reconstruction for eukaryotic organisms remains a much more complicated problem. Despite significant progress in genome sequencing, the annotation of eukaryotic genomes remains a complicated problem. Even finding the ORFs, a key component of gene identification, is still a very difficult task. A comprehensive understanding of the complicated structure of eukaryotic genomes will require the integration of sequencing information with genetic, biochemical, structural, and evolutionary data. It will require developing new bioinformatics tools and discovering new algorithms, and, most likely, it will take years of research in both dry and wet labs.

In contrast, a good deal of information about the sequences and expression patterns of eukaryotic genes has been accumulated in numerous databases of expressed sequence tags (ESTs). (See, for example Unigene EST, dbEST, STACK, SAGE, DOTS, trEST, XREFdb, in addition to a number of tissue-specific databases, such as PEDB.) A significant amount of human EST data has already been carefully analyzed, classified, annotated, and mapped to chromosomes. Currently, there are over 1,000,000 human ESTs available in public databases representing 50-90% of all human genes. (Electrophoresis, 1999, Feb. 20(2):223-9). It is generally believed, however, that EST sequences are inferior to genomic DNA sequences in terms of their quality and degree of representativeness.

The technology known as Metabolic Reconstruction was developed by Dr. Evgeni Selkov and co-workers at the Argonne National Laboratory. Metabolic Reconstruction was developed to study an organism's metabolism by using its genome sequence. (Selkov, et al., (1997) A reconstruction of the metabolism of *Methanococcus jannaschii* from sequence data. Gene, 197, GC11-26).

Traditionally, it has not been considered feasible to study metabolism based on EST data. Such an approach, however, would be very useful for comparative analyses of complex eukaryotic genomes. First, generation of a complete set of ESTs is at least an order of magnitude less expensive than whole genome sequencing. Second, there is a great deal of processed EST data freely available to the scientific community. Currently there are only a few complete eukaryotic genomes currently available to the public, but there are sufficient EST data for several dozens of species. Third, and most important, ESTs represent genes that are expressed at specific times in specific tissues. In the present invention, expressed sequence tag (EST) data were used rather than genomic sequences.

SUMMARY OF THE INVENTION

The process of the present invention, referred to as System Reconstruction, integrates data on organism- and tissue-specific biochemical pathways, genome sequences, conditional gene expression, and genetic polymorphisms with clinical manifestations of diseases and other clinical traits. As a result, a network of interconnected functional pathways (a Functional or System Model) is constructed in which elements are linked to appropriate molecular data (ORFs, ESTs, SNPs, etc.) and annotated with relevant clinical information.

In one aspect, the present invention ascertains necessary functions involved in a particular metabolic pathway.

In another aspect, the present invention provides a visual overview of expressed genes associated with a particular pathway specific for normal and abnormal human tissues.

In another aspect, the present invention provides a method for determining and identifying the ORFs involved in those pathways.

In another aspect, the present invention provides a method for comparing System Reconstructions made for normal and diseased organs or tissues, thus providing important information about possible regulatory mechanisms and potential drug targets.

In another aspect, the present invention provides a method for comparing the reconstructions made for the same tissue at different developmental stages, thus providing information about the developmental timing of gene expression and revealing possible targets for gene therapy.

In another aspect, the present invention provides a method for mapping single nucleotide polymorphism (SNP) sites to corresponding metabolic genes and/or predicted ORFs, thus providing physiological insights into associations of SNPs with unknown phenotypes.

DESCRIPTION OF THE PREFERRED EMBODIMENTS

A bioinformatics approach called System Reconstruction is used to integrate clinical information with high-throughput molecular data. System Reconstruction technology is described in co-pending U.S. Provisional Patent Application Ser. No. 60/299,040, and U.S. patent application Ser. No. 10/174,762, entitled "System Reconstruction: Integrative Analysis of Biological Data," filed on Jun. 18, 2002, both of which are incorporated herein by reference. In the core of this approach, a collection of human tissue-specific and condition-specific biochemical pathways are linked by common intermediates into maps or models. These models serve as a framework to integrate complementary types of high-throughput data and to establish mechanisms underlying clinical manifestations of diseases.

Figure 1:
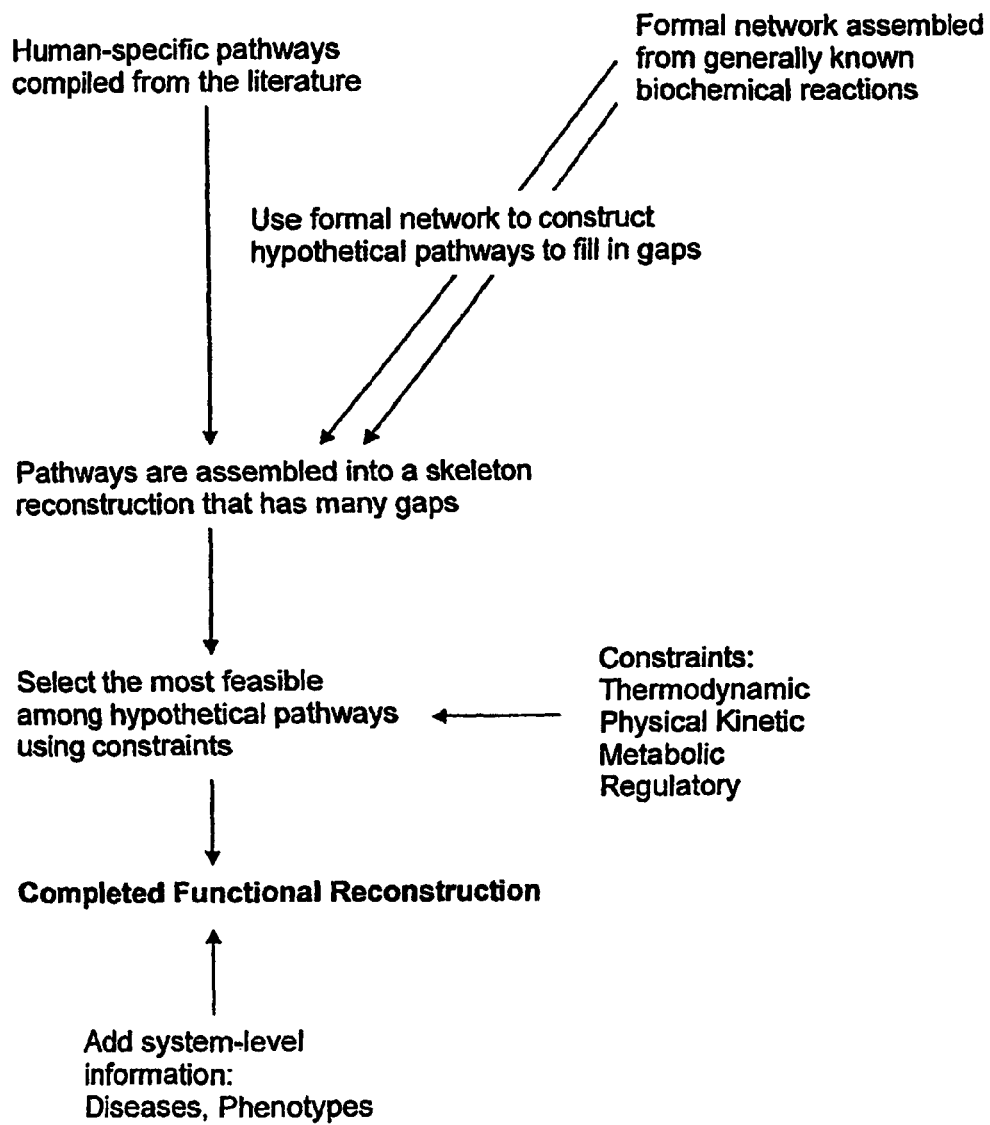
FIG. 1 is a schematic overview of the process of System Reconstruction.

The present invention creates a system that allows building human-specific system-level models of biochemistry. In summary, information regarding human-specific pathways is collected. The pathways are linked to functional information, disease manifestations, and high-throughput data. Finally, pathways are connected to each other and linked to relevant information to form a functional model. These models can be used, for example, as skeletons for further integration of high-throughput data, for deciphering mechanisms of diseases, for predicting drug metabolism and toxicity, and the like. System Reconstruction is a complex multi-step process that involves assembling a collection of human-specific pathways and results in fully annotated interactive maps of specific metabolic systems. See FIG. 1.

The process of System Reconstruction generally starts with the creation of a collection of metabolic pathways. Pathways that are human-specific and in the form in which they occur in humans are included. Building such a collection is achieved through a multi-level annotation process. Starting with a collection of identified metabolic pathways from mammals and non-mammals, the pathways are divided into categories based on relevance. For example, pathways are ranked according to the probability of their relevance in human metabolism. The most relevant pathways include multi-step mammalian pathways in which all of the reactions are catalyzed by identified human enzymes or at least enzymes that have ORF candidates in the human genome. Less relevant pathways include, for example, pathways in which the necessary enzymes have not been identified in humans, and single step pathways. Information such as clinical data and scientific literature is reviewed to confirm which pathways are, in fact, present in humans.

In addition to creating a collection of human specific pathways, the process of annotation yields important functional data about each pathway and its elements. In order to structure this information, a pathway is described as a hierarchy of "biochemical units." These units comprise the pathway itself, individual steps that make up the pathway, chemical compounds, reactions, and "enzymatic functions" that are involved in each step. "Enzymatic functions" are related, in turn, to molecular species-specific proteins and genes. In a process called structured annotation, links are established between particular "biochemical units" and specific categories and instances in other data fields, discussed in greater detail below. Practically, this is achieved by filling in annotation tables associated with each biochemical unit. Examples of fields in these tables include: organ and tissue localization of the unit; intracellular localization and/or compartmentalization; existence and subcellular localization of the unit in other organisms; connection of the unit with inherited and common diseases and other functional disorders; type of relationship between the unit and a disease (e.g., cause, manifestation, etc); references on the information source, and the like.

Structured annotation allows the organization of heterogeneous data and the development of queries and computer algorithms that can track explicit and implicit links among these data. Some examples include finding compounds, enzymes, reactions, and pathways that are directly linked in a particular unit; automatically interconnecting pathways and reactions into networks based on shared intermediates or other links; establishing constraints on pathway interactions based on sub-cellular localization of their components; finding pathways, reactions compounds, and enzymes related to a disease, its causes or manifestations, and interconnecting such elements into a "disease network"; finding diseases related by common pathways, reactions, or compounds; finding alternative pathways for degradation or biosynthesis of specific compounds, to circumvent certain enzymes, and the like.

In order to organize the information collected in the process of reconstruction, a relational database has been developed using Oracle RDBMS. Unlike many biomedical databases which are centered around a certain theme (e.g. sequences, proteins, biochemical reactions, etc.), the database developed in the present invention is a polythematic database that is built around several central data entities and relations among them. These entities are enzymes; compounds; reactions; pathways; genes; and diseases. This core architecture provides multiple "linking portals" for including other often heterogeneous data such as gene expression, protein interactions, metabolite profiles, etc. Once linked, these data become a part of a large system-level picture.

The next step is building of the functional models of specific categories of human metabolism, diseases, and other system-level reconstructions. Two important steps here are (1) to select a subset of the relevant pathways, and (2) to link them into metabolic networks. Selection of pathways is done by a set of "SELECT . . . FROM . . . WHERE . . . " type queries, relying on the information collected in structured annotation tables discussed above. The information on links among pathways is implicitly contained in the database. Whenever two pathway records share a common intermediate, or when an intermediate in one pathway occurs as a regulatory factor in a record for an enzyme from another pathway, a link is generated between the two pathways.

Figure 2:
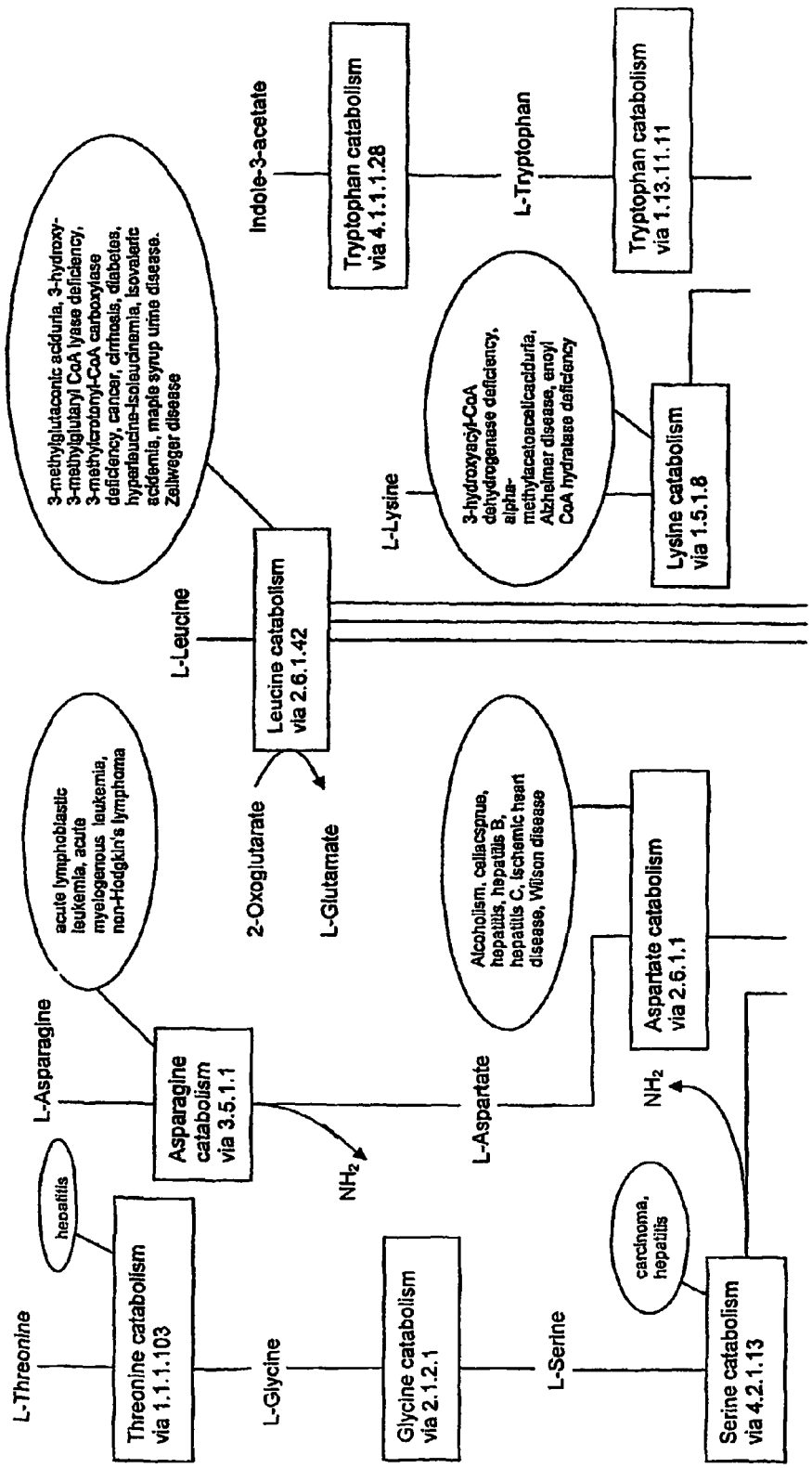
FIG. 2 illustrates a portion the reconstruction of human amino acid metabolism.
Figure 3:
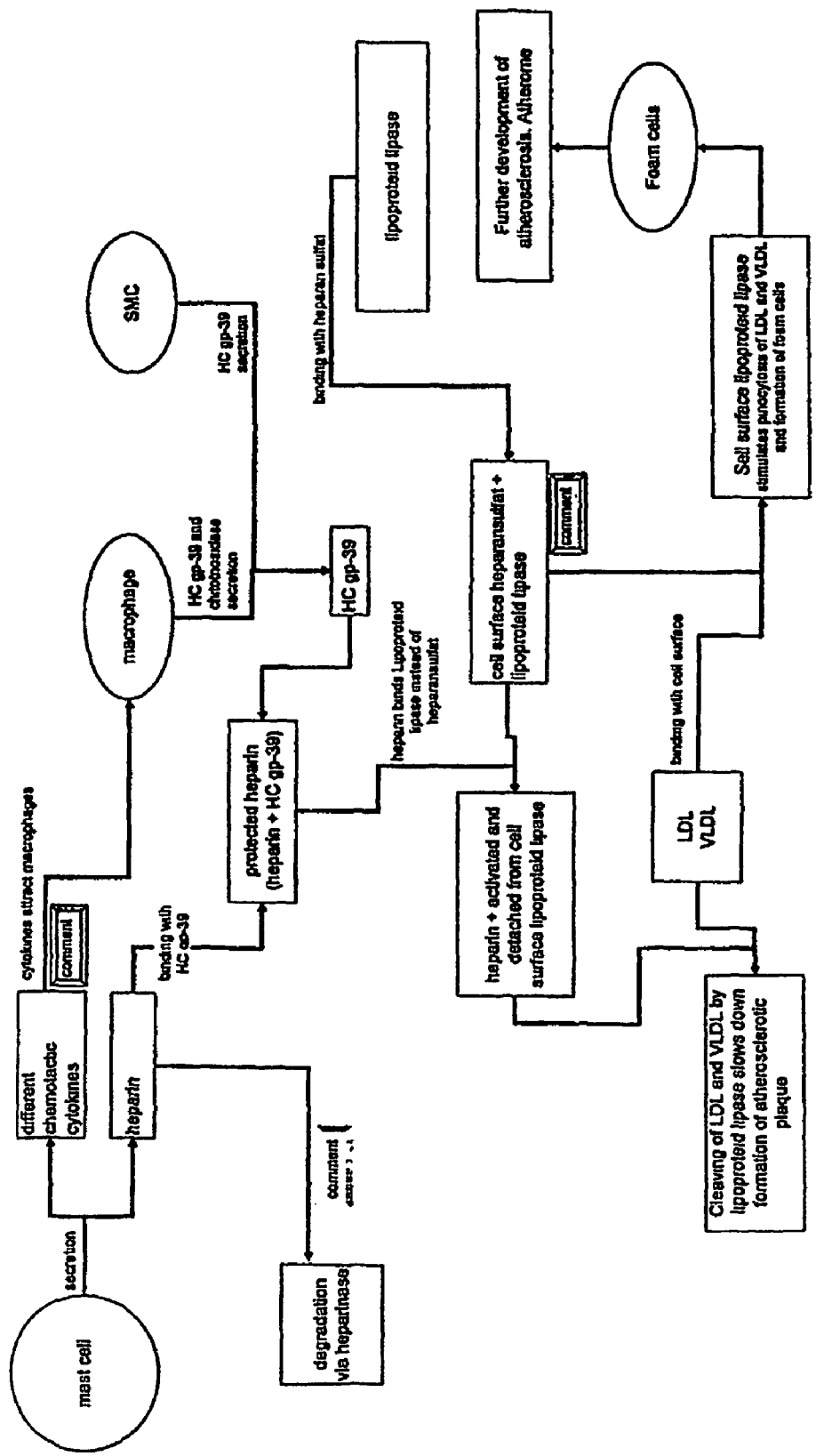
FIG. 3 is a flow diagram illustrating the relationship between pathways involved in atherosclerosis.

The technology of the present invention was used to build the System Reconstruction of amino acid metabolism in human, a portion of which is illustrated in FIG. 2. The reconstruction consists of two major parts: amino acid biodegradation and amino acid biosynthesis. The user interface of the reconstruction is an interactive map showing pathways involved in amino acid metabolism. Pathways are interconnected into a network by shared metabolites. By clicking the mouse on a pathway, a user can access the pathway page showing detailed diagrams with reactions and enzymes. From this page, related pages for enzymes and reactions can also be accessed. In addition, pathway notes which describe diseases that are linked to the pathway are accessible from this page. An enzyme page contains the enzyme name and its synonyms, links to gene pages for genes related to the enzyme, a list of reactions and pathways in which the enzyme is involved, and notes on the involvement of the enzyme in human diseases.

One feature of the reconstruction is the incorporation of human diseases. By activating a link to diseases, a user can see lists of diseases associated with the pathway. From these lists, pages for individual diseases can also be accessed. These pages contain lists of enzymes, reactions, and pathways that have been linked to a disease. In addition, one can view notes describing various aspects of a disease mechanism, its metabolic causes, and/or its manifestations.

One aspect of the System Reconstruction technology of the present invention is that it uses organism-specific pathways to build maps. This allows the imposition of a condition of self-consistency on the resulting networks. This means that each metabolite should either be essential for the organism (e.g., consumed through food) or there should be a pathway that produces it. In other words, if there is a gap between two nonessential compounds, this implies a lack of knowledge and serves to direct further research.

This allows the prediction of the existence of an enzyme function in an organism even if organism-specific genes or proteins have not been identified. For example, when there is a clear gap between two metabolites in the reconstruction that cannot be filled in by any of the described enzymes, it is predicted that there is at least one undescribed enzyme that bridges this gap. In the present reconstruction of amino acid metabolism in humans, several human enzymes were identified that had not been previously identified in the human genome. These enzymes were identified because their functions were required by the logic of the metabolic map. Consequently, human genes for these enzymes were proposed through thorough similarity searches of the human genome and by studying human ESTs.

The self-consistency condition also helps eliminate pathways that might be incorrectly assigned merely on the basis of human enzymes having been identified. One example can be illustrated with phenylalanine biosynthesis. It is well known that humans cannot synthesize this essential amino-acid. However, there is a human enzyme, aspartate transaminase (EC 2.6.1.1), that could potentially synthesize phenylalanine from phenylpyruvate. Simply superimposing the human enzyme onto a general metabolic map would lead to the incorrect conclusion that there is a human pathway for phenylalanine biosynthesis. In contrast, the self-consistent reconstruction of the present invention shows that the absence of phenylpyruvate, the substrate for aspartate transaminase, makes biosynthesis of phenylalanine improbable in humans.

The following examples illustrate pathways in which chitinase is involved. These pathways have been elucidated through the use of the System Reconstruction technology. The technology of System Reconstruction is described in copending U.S. Provisional Patent Application Ser. No. 60/299,040 and U.S. patent application Ser. No. 10/174,762, entitled "System Reconstruction: Integrative Analysis of Biological Data," filed on Jun. 18, 2002, both of which are incorporated herein by reference.

Example 1

Stabilization of Heparin for Treatment of Arteriosclerosis

HC gp-39, a protein of the chitinase family, can be used in combination with heparin to treat arteriosclerosis. Addition of HC gp-39 may stabilize heparin and increase its effectiveness.

Heparin appears to play a role in arteriosclerosis. Data shows that patients suffering from arteriosclerosis have decreased heparin levels. Therapeutic treatment with heparin is used to reduce the risk of infarction and stroke. Heparin is also used as an anti-coagulant. It activates antithrombin-III. Additionally, low molecular weight heparin is used for the treatment of lipid metabolism disorders as an agent that activates lipoprotein lipase.

Under normal conditions, lipoprotein lipase is localized on the cell surface, including the surface of endothelial cells in blood vessels. The binding of heparan sulfate to lipoprotein lipase is responsible for the retention of lipoprotein lipase on the cell surface. While bound to the cell surface, lipoprotein lipase is not enzymatically active, but serves as a receptor, binding low density and very low density lipoproteins (LDL and VLDL). This binding leads to the cellular uptake of lipoproteins. (PMID 10532590). Development of arteriosclerosis is characterized by the emergence of so-called "foam cells" that form due to an excess of lipoproteins being absorbed into the cell through pinocytosis.

Heparin has a higher affinity for lipoprotein lipase than does heparan sulfate. With the exchange of heparin for heparan sulfate binding to lipoprotein lipase, the lipoprotein lipase is activated and released from the cell surface and into the intercellular space and to the blood. (PMID 11427199). While the binding of heparin activates lipoprotein lipase, in the absence of heparin, even if lipoprotein lipase is released from the cell surface, it remains inactive. (PMID 10760480).

The binding of heparin to lipoprotein lipase results in several positive therapeutic effects. First, the uptake of lipoproteins by cells is decreased and, therefore, further formation of "foam cells" is prevented. Second, heparin-bound lipoprotein lipase regains its catalytic activity (PMID 210908, 698674) and starts to degrade LDL and VLDL in the intercellular space and in the blood. An excess of LDL and VLDL in the blood leads to the formation of atherosclerotic plaques. In contrast, degradation of LDL and VLDL by lipoprotein lipase leads to the formation of fatty acids that are eventually processed in the liver. Therefore, the degradation of LDL and VLDL by lipoprotein lipase helps prevent the development of arteriosclerosis.

As mentioned above, patients with arteriosclerosis are often treated with heparin. Free heparin is thought to be degraded by heparinase. A full length human heparinase enzyme has not been isolated. Human heparinase is known only by fragments of its sequences (NCBI protein # AAE10146-10153, AAE13758-13770, AAE67749-67785). While the enzymatic activity of human heparinase has not been directly studied, other known heparinases belong to the class of enzymes known as lyases (EC number 4.2.2.7, "Eliminative Cleavage Of Polysaccharides Containing 1,4-Linked Glucuronate Or Iduronate Residues And 1,4-Alpha-Linked 2-Sulfoamino-2-Deoxy-6-Sulfo-D-Glucose Residues To Give Oligosaccharides With Terminal 4-Deoxy-Alpha-D-Gluc-4-Enuronosyl Groups At Their Non-Reducing Ends"). Based on similarities to known heparinases, it is likely that human heparinase interacts with heparin through binding to its non-reducing end and degrades heparin.

Figure 4:
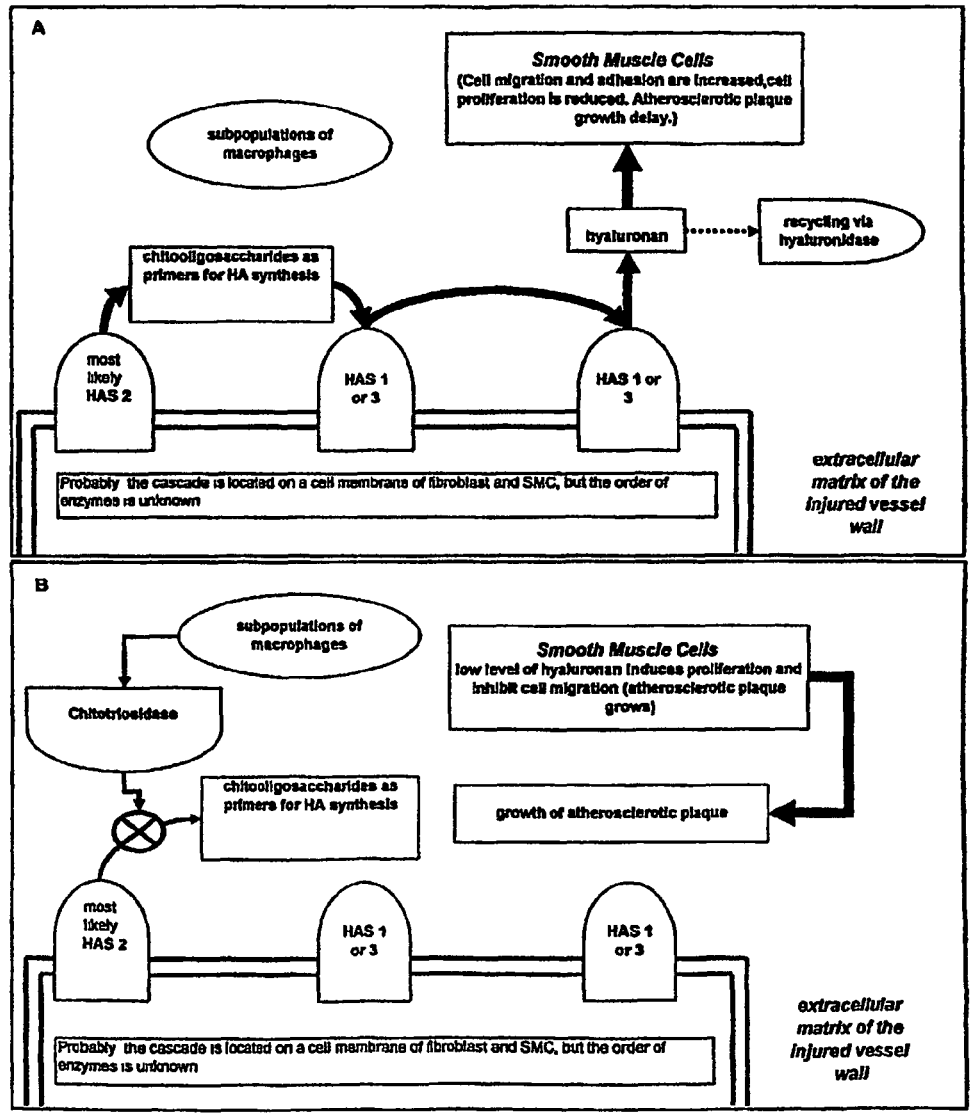
FIG. 4A is a flow diagram illustrating the pathway of chitotriosidase function in atherogenesis when chitotriosidase activity is suppressed.
FIG. 4B is a flow diagram illustrating the pathway of chitotriosidase function in atherogenesis when chitotriosidase activity is present.

HC gp-39, a protein of chitinase family, can also bind to heparin. (Medline 96325055). The binding of heparin (or heparin analogs) to HC gp-39 may protect heparin from degradation by heparinase. (FIG. 4). By protecting heparin from degradation, the period of time for which heparin is active is extended. The use of HC gp-39 in combination with heparin (or its therapeutic analogs) may enhance the effectiveness of heparin in the treatment of arteriosclerosis.

Currently, there is no direct evidence regarding the way in which HC gp-39 binds to heparin. It is known, however, that some hydrolases, which are close to chitinases, bind their substrates at the non-reducing end of the substrate. HC gp-39, therefore, may similarly bind to the non-reducing end of heparin. This binding would protect heparin from degradation by heparinase. The HC gp-39 homolog from pig smooth muscle culture (porcine gp38k) has been studied in greater detail. (Shackelton et al., JBC 270(22), 1995). HC gp-39 shows 84.6% homology with gp38k (DNAstar). The site of heparin binding on gp38k (residues 144-149, RRDKRH) is similar to a putative heparin binding site on HC gp-39 (RRD-KQH) in which glutamine is substituted for arginine in the human protein.

Example 2

Tissue Remodeling

Figure 5:
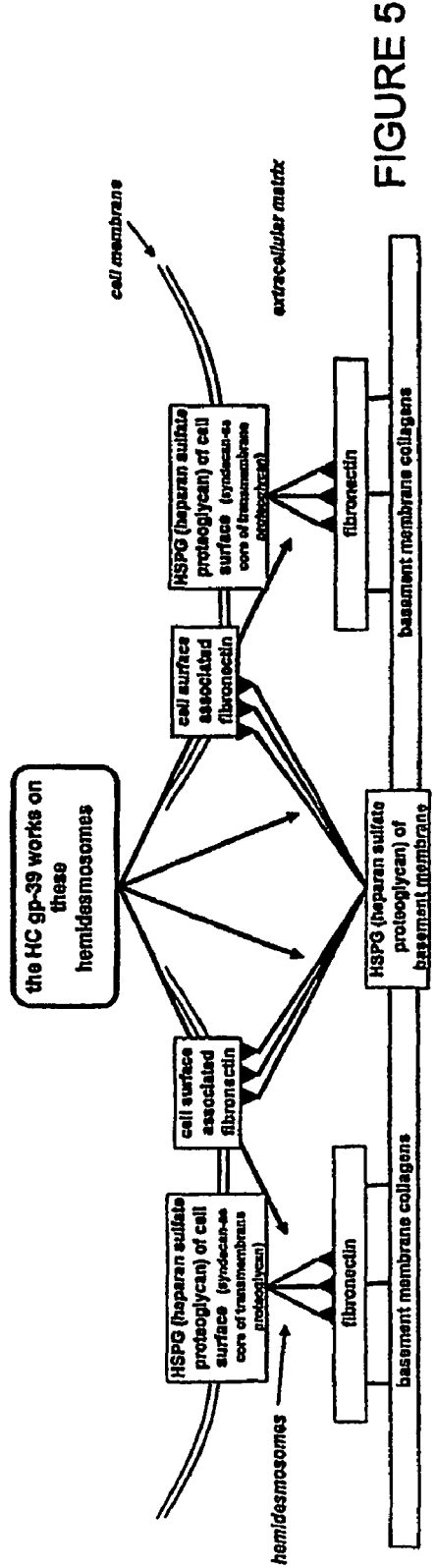
FIG. 5 is a schematic view of various interactions between the cell surface and the extra-cellular matrix.

In most tissues, cells are connected through a membrane-based complex of polysaccharides and through membrane-linked proteins known as the glycocalix and the extra-cellular matrix. Heparan sulphate is one of the most important components of both the glycocalix and the extra-cellular matrix. Heparan sulphate binds to fibronectin and other structural proteins; this binding is required for the fixation of cells within tissues and determines tissue structure. (FIG. 5). The mechanisms of binding between heparan sulphate and fibronectin have been studied, and this binding is significant in the positioning of fibroblasts, epidermal cells, and endothelium, (PMID 3917945, 8838671, 10899711). It has also been shown that heparan sulphate binds to thrombospondin during the establishment of the intercellular contacts (PMID 1940309), and that there is a correlation between cell aggregation and the binding of heparan sulphate with syndecan-1 (PMID 7890615).

HC gp-39, a protein of the chitinase family, has a higher affinity for, heparan sulphate than does fibronectin. (Medline 96325055). HC gp-39 may compete with fibronectin for the binding of heparan sulphate. If HC gp-39 binds to heparan sulphate replacing fibronectin, intercellular bonds and the structural components which retain tissue structure can be relaxed. Such relaxing is required for successful tissue remodeling and regeneration. By increasing the local concentration of HC gp-39, and thereby locally relaxing structural elements of a tissue, tissue remodeling and regeneration can be stimulated. Such an application would be useful in such areas as wound healing and joint alterations due to arthritis.

Example 3

Arteriosclerosis

Hyaluronic acid (HA) binds to smooth muscle cells and prevents their proliferation. Proliferation of smooth muscle cells in arteriosclerosis leads to the growth of the arteriosclerotic plaque. Therefore, HA is a factor that helps contain the disease. Chitotriosidase, or chitinase 1, may restrict the synthesis of HA by degrading the chitin primers necessary for HA formation. Therefore, chitotriosidase facilitates the growth of arteriosclerotic plaques. Suppression of the activity of chitotriosidase may be useful in the treatment of atherosclerosis. (See FIGS. 4A and 4B).

Hyaluronic acid is involved in various processes of tissue repair and remodeling. In particular, HA plays a role in the regulating the migration and proliferation of smooth muscle cells which are critical in the pathogenesis of cardiovascular diseases. HA acts as a negative regulator of the proliferation of smooth muscle cells induced by platelet-derived growth factor (PDGF) and as a positive regulator of PDGF-induced migration. (PMID: 9678773, 8842351, 7568237).

Uncontrolled proliferation of smooth muscle cells facilitates the growth of atherosclerotic plaques. As cells start to actively absorb lipid particles, turning into "foam cells", the cells form the core of the plaque. Additionally, proliferation of smooth muscle cells leads to the enlargement of the formation and the isolation of the "foam cells" by covering them with new layers of smooth muscle cells. This further leads to the formation of atheroma, or the degeneration of the artery lining. Drugs that reduce smooth muscle cell proliferation are often used as a part of atherosclerosis therapy. Most of these drugs, however, are hormones that have many undesirable side-effects and may be restricted in their use.

HA is synthesized on the extracellular side of the plasma membrane of various cell types, including smooth muscle cells and endothelial cells. (PMID: 10493913). Apparently, fibroblasts provide a source for much of the HA implicated in atherosclerotic damage. (See e.g., PMID: 11378333, 11327061, 11171074). HA synthesis is catalyzed by the enzyme hyaluronan synthase (HAS). Presently, three human genes for this enzyme have been identified: HAS-1, HAS 2, HAS 3, mapping to chromosomal regions 19g13.3-q13.4, 8q24.12, and 16q22.1, respectively. HAS is a plasma membrane proteins.

It has been shown that human hyaluronan synthase is highly homologous to the enzymes from other organisms including glycosaminoglycan synthase from Xenopus (DG42). (PMID: 8798544, 8798477). It has been shown that DG42 and its analogs from zebrafish and mouse exhibit chitin oligosaccharide synthase activity. Furthermore, addition of purified chitinase to zebrafish cell extracts leads to significant (up to 87%) reduction in the synthesis of HA. Based on these data, it is thought that chitin oligosaccharides serve as primers for hyaluronic acid synthesis. (PMID: 8643441).

Chitotriosidase (EC 3.2.1.14) and HC gp-39 expressed by macrophages in the area of atherosclerotic damage have been found in the blood vessel wall matrix. It has been suggested that chitotriosidase recognizes the HA primer as its own substrate and, therefore, interferes with the synthesis of HA. (PMID: 10073974).

The mechanism by which chitotriosidase participates in the process of regulating proliferation and migration of smooth muscle cells may be based on its enzymatic activity with respect to chitin-like oligosaccharides that serve as primers for HA synthesis. The cleavage of these primers by chitotriosidase may lower the local concentration of HA, therefore, leading to an increase in cell proliferation causing further damage to the blood vessel wall.

Example 4

Cosmetics

Glycosaminoglycans are widely used in dermatology and cosmetology for healing and regeneration of skin damage due to trauma, surgery, or aging. In the past decade, a number of cosmetics and therapeutic treatments containing glycosaminoglycans were developed and marketed for topical use and for injection. Compositions have included glycosaminoglycans such as chitosan, gyaluonic acid, heparin, heparan sulphate, and others. The inclusion of human lectin HC gp-39 into topical compositions with glycosaminoglycans may accelerate and prolong skin improvement. (FIG. 5).

Addition of HA to the extra-cellular matrix causes hydratation and increases turgor in a tissue. As discussed above, HA is also one of the important factors in tissue remodeling, as it interacts with a number of proteins and non-protein components of extra-cellular matrix to form a scaffold for the formation of cell layers. HA stimulates the expression of metal proteases in the extra-cellular matrix, for example, elastase-like endopeptidases expressed in fibroblasts and keratinocytes. Both of these cell types receptors for binding hyaluronic acid which is needed for tissue remodeling.

The use of HC gp-39 in combination with hyaluronic acid, may play a function similar to lectin, having a loosening effect on both protein and glycosaminoglycan elements of the extra-cellular matrix. Treatment with HC gp-39 and HA would preferably be followed by treatment with fibroblast growth factor (FGF) and insuline-like growth factor (IGF) in order to stimulate expression of HAS1, HAS2 and HAS3 for endogenous synthesis of HA. (FIGS. 4A and 4B).

Therapeutic or preventive treatment with HA is especially important for elderly patients or patients with age-related conditions because the level of endogenous HA diminishes with age. (With age, the number of lipid-filled macrophages raises causing an increase in the concentration of chitotriosidase and, correspondingly, the depletion of endogenous HA).

HA is also capable of deep penetration into the epidermis and may be used as a vehicle for drug delivery.

Example 5

Parkinson's Disease

One of the treatments for Parkinson disease includes transplantation of neurons from the substantia nigra of 6-10 week old embryos. The effectiveness of this treatment depends on the successful incorporation of the transplanted tissue. Currently employed techniques show fairly low success rate. (Kupsch A. et al., Nervenarzt, 1991, Bd. 62, S. 80-91; Landvall O., Europ. Neurol., 1991, Vol. 31, Suppl. 1, P. 17-27). The low success rate is related to rejection of the transplant, usually within several months after surgery. It has been shown that successful transplantation can be achieved with the addition of embryonic neuro-ectodermal cells of. *Drosophila melanogaster* into the transplant tissue. (PMID: 9532720; PMID: 9449456). These cells are known to express a number of growth factors and remodeling factors, including DS47, which is homologous to human protein HC gp-39.

Incorporation of a transplant is related to the processes of tissue remodeling. Integration of transplanted cells into a damaged tissue and differentiation of the transplanted cells is necessary for restoring the function of the damaged tissue. These processes are related to tissue remodeling, and remodeling factors play a significant role in the interaction of transplanted cells with the extracellular matrix and the cells of the recipient. Often rejection of the transplant is not due to an immune response in the recipient, but rather to the lack of tissue integration caused by the formation of glial scar tissue and the lack of blood vessel in-growth into the transplanted tissue. One apparent reason is the low activity of remodeling factors in the recipient tissue. In particular, the rejection it may be related to age-dependent weakening of remodeling capabilities.

It may be possible to regulate tissue remodeling upon transplantation by changing the local concentration of remodeling factors, including proteins belonging to chitinase family such as HC gp-39. Activity of brain chitinases should be related to microglial cells that are descendants of blood monocytes. Neutral cells of a transplant, on the other hand do not accumulate enough remodeling factors due to their nature. The significant increase in transplant integration success rates by incorporating Drosophila embryonic cells suggests that these cells actively express remodeling factors that are closely related to such factors in humans. It is known that four proteins belonging to the chitinase family are expressed in the human brain (HC gp-39, chitotriosidase, YKL 39, and FLJ12549). There is also expression of chitinase-like proteins in the embryonic cells of *Drosophila*. These proteins lack catalytic activity, but are capable of binding with proteoglycans of the extracellular matrix. One of the *Drosophila* proteins shows slightly homologous to human HC gp-39. (PMID 7875581).

Those skilled in the art will readily understand that variations of the materials, conditions, and processes described in these examples can be used. All references cited herein are incorporated by reference in their entirety.

What is claimed is:

1. A computer-implemented method for reconstructing human metabolism in a non-disease state and a disease state, said method comprising:
   (a) collecting metabolic data for said non-disease and disease states;
   (b) linking the data into metabolic pathways using a relational database;
   (c) ranking the metabolic pathways based on their relevance to human metabolism, wherein the ranking of the metabolic pathways comprises assigning each pathway to one of the following categories, from the most relevant to the least relevant to human metabolism:
      (i) a multi-step pathway wherein all of the reactions are catalyzed by known human enzymes and/or enzymes that have open reading frame (ORF) candidates in the human genome;
      (ii) a multi-step pathway wherein not all of the reactions are catalyzed by known human enzymes and/or enzymes that have ORF candidates in the human genome; and
      (iii) a single step pathway;
   (d) linking said ranked metabolic pathways to functional information, disease manifestations and/or high-throughput screening information;
   (e) identifying interconnections between the ranked metabolic pathways; and
   (f) reconstructing human metabolism in said non-disease and disease states on the basis of information obtained in steps (a) through (e).

2. A computer-implemented method for identifying a human drug target, said method comprising:
   (a) collecting metabolic data for a non-disease state and a disease state;
   (b) linking the data into metabolic pathways using a relational database;
   (c) ranking the metabolic pathways based on their relevance to human metabolism, wherein the ranking of the metabolic pathways comprises assigning each pathway to one of the following categories, from the most relevant to the least relevant to human metabolism:
      (i) a multi-step pathway wherein all of the reactions are catalyzed by known human enzymes and/or enzymes that have open reading frame (ORF) candidates in the human genome;
      (ii) a multi-step pathway wherein not all of the reactions are catalyzed by known human enzymes and/or enzymes that have ORF candidates in the human genome; and
      (iii) a single step pathway;

(d) linking said ranked metabolic pathways to functional information, disease manifestations and/or high-throughput screening information;
(e) identifying interconnections between the ranked metabolic pathways;
(f) reconstructing human metabolism in said non-disease and disease states on the basis of information obtained in steps (a) through (e); and
(g) identifying a human drug target by comparing differences between said non-disease and disease states using the reconstruction of step (f).

3. The method of claim 1, wherein said metabolic data comprises expressed sequence tag data.

4. The method of claim 1, wherein said metabolic data comprises biochemical units comprising metabolic steps, chemical compounds, reactions and/or enzymatic functions.

5. The method of claim 4, wherein said enzymatic functions comprise genes and proteins.

6. The method of claim 4, wherein each of said biochemical units is linked to an annotation table, said annotation table comprising at least one field.

7. The method of claim 6, wherein said at least one field is selected from the group consisting of organ localization, tissue localization, intracellular localization, intracellular compartmentalization, subcellular localization in another organism, a relationship to a disease, and a reference to an information source.

8. The method of claim 2, wherein said metabolic data comprises expressed sequence tag data.

9. The method of claim 2, wherein said metabolic data comprises biochemical units comprising metabolic steps, chemical compounds, reactions and/or enzymatic functions.

10. The method of claim 9, wherein said enzymatic functions comprise genes and proteins.

11. The method of claim 9, wherein each of said biochemical units is linked to an annotation table, said annotation table comprising at least one field.

12. The method of claim 11, wherein said at least one field is selected from the group consisting of organ localization, tissue localization, intracellular localization, intracellular compartmentalization, subcellular localization in another organism, a relationship to a disease, and a reference to an information source.

13. A computer-implemented method for predicting the existence of a novel human enzyme, said method comprising:

(a) collecting metabolic data in non-disease and disease states;
(b) linking the data into metabolic pathways using a relational database;
(c) ranking the metabolic pathways based on their relevance to human metabolism, wherein the ranking of the metabolic pathways comprises assigning each pathway to one of the following categories, from the most relevant to the least relevant to human metabolism:
(i) a multi-step pathway wherein all of the reactions are catalyzed by known human enzymes and/or enzymes that have open reading frame (ORF) candidates in the human genome;
(ii) a multi-step pathway wherein not all of the reactions are catalyzed by known human enzymes and/or enzymes that have ORF candidates in the human genome; and
(iii) a single step pathway;
(d) linking said ranked metabolic pathways to functional information, disease manifestations and/or high-throughput screening information;
(e) identifying interconnections between the ranked metabolic pathways;
(f) reconstructing human metabolism in said non-disease and disease states on the basis of information obtained in steps (a) through (e); and
(g) predicting the existence of a novel human enzyme by detecting a gap between non-essential metabolites that cannot be filled by any known human enzyme from the reconstructing of step (f).

14. The method of claim 13, wherein said metabolic data comprises expressed sequence tag data.

15. The method of claim 13, wherein said metabolic data comprises biochemical units comprising metabolic steps, chemical compounds, reactions and/or enzymatic functions.

16. The method of claim 15, wherein said enzymatic functions comprise genes and proteins.

17. The method of claim 15, wherein each of said biochemical units is linked to an annotation table, said annotation table comprising at least one field.

18. The method of claim 17, wherein said at least one field is selected from the group consisting of organ localization, tissue localization, intracellular localization, intracellular compartmentalization, subcellular localization in another organism, a relationship to a disease, and a reference to an information source.

* * * * *